(12) United States Patent
Gibbs et al.

(10) Patent No.: US 8,212,190 B1
(45) Date of Patent: Jul. 3, 2012

(54) DECORATIVE HANDLE SHEATH AND ASSOCIATED METHOD

(76) Inventors: Priscilla Gibbs, Bronx, NY (US); Evangeline Jenkins, Staten Island, NY (US)

(*) Notice: Subject to any disclaimer, the term of this patent is extended or adjusted under 35 U.S.C. 154(b) by 367 days.

(21) Appl. No.: 12/690,578

(22) Filed: Jan. 20, 2010

Related U.S. Application Data

(60) Provisional application No. 61/205,363, filed on Jan. 20, 2009.

(51) Int. Cl.
*H05B 3/10* (2006.01)
*H05B 1/02* (2006.01)

(52) U.S. Cl. ..... 219/547; 219/209; 219/264; 219/463.1; 219/513; 219/518

(58) Field of Classification Search ............. 219/547, 219/209, 264, 463.1, 513, 518
See application file for complete search history.

(56) References Cited

U.S. PATENT DOCUMENTS

| | | | |
|---|---|---|---|
| 3,710,985 A * | 1/1973 | Baum | 222/146.3 |
| 3,822,434 A * | 7/1974 | Mahoney | 15/160 |
| 5,493,756 A | 2/1996 | Shanok et al. | |
| 5,659,927 A | 8/1997 | Shanok et al. | |
| 5,740,587 A | 4/1998 | Onai et al. | |
| 6,660,974 B2 * | 12/2003 | Faries et al. | 219/400 |
| 2010/0003067 A1 * | 1/2010 | Shaw et al. | 401/206 |

* cited by examiner

*Primary Examiner* — Nitin Parekh

(57) ABSTRACT

A protective handle sheath including a body adapted to wrap about the existing appliance handle, a heat-activated anti-bacterial agent impregnated within the body, and first and second hook and loop strips attached to oppositely situated first and second longitudinal edges of the body respectively. The first and second hook and loop strips generate heat when engaged with each other such that the heat is transferred through the body and thereby transforms the anti-bacterial agent from an inactive state to an active state. In this manner, the anti-bacterial agent is released out from an interior of the body and thereby adapted to directly contact an outer surface of the existing appliance handle. Conversely, the anti-bacterial agent automatically returns to an inactive state when the first hook and loop strip is separated from the second hook and loop strip. Thus, the inactive anti-bacterial agent is absorbed into the interior of the body.

13 Claims, 7 Drawing Sheets

DECORATIVE HANDLE SHEATH AND ASSOCIATED METHOD

CROSS REFERENCE TO RELATED APPLICATIONS

This application claims the benefit of U.S. Provisional Application No. 61/205,363, filed Jan. 20, 2009, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to home decor and, more particularly, to a decorative handle sheath for simultaneously protecting and ameliorating appliance handle appearances.

2. Prior Art

Nothing compares to the comforts of home when looking for a respite from the constant demands of on-the-go living. When busy days are done, walking into one's own personally decorated sanctuary can foster a feeling of well-being and comfort. While many want their homes to reflect exquisite style, they also desire a casual tone that is inviting to them as well as to their guests. Professional interior designers offer many suggestions to achieve these effects, including the use of bright colors to liven the atmosphere, hanging artwork, prints and posters to inject character, and adding vintage sconces to create a relaxing ambiance. A room that is not exempt from fashionable decor is the household kitchen. The epicenter of a plethora of activities ranging from the preparation and eating of meals to even homework sessions at the kitchen table, much time is spent in this area of the home, and consumers seek to make the kitchen as inviting as their living rooms.

Accordingly, a need remains for an apparatus in order to overcome the above-noted shortcomings. The present invention satisfies such a need by providing a decorative handle sheath that is convenient and easy to use, lightweight yet durable in design, versatile in its applications, and designed for providing a user with a means to simultaneously protect and ameliorate the aesthetics of his or her handles.

BRIEF SUMMARY OF THE INVENTION

In view of the foregoing background, it is therefore an object of the present invention to provide a protective handle sheath for covering an existing appliance handle. These and other objects, features, and advantages of the invention are provided by a protective handle sheath including a body adapted to wrap about the existing appliance handle, a heat-activated anti-bacterial agent impregnated within the body, and first and second hook and loop strips attached to oppositely situated first and second longitudinal edges of the body respectively.

Advantageously, the first and second hook and loop strips generate heat when engaged with each other such that the heat is transferred through the body and thereby transforms the anti-bacterial agent from an inactive state to an active state. In this manner, the anti-bacterial agent is released out from an interior of the body and thereby adapted to directly contact an outer surface of the existing appliance handle. Conversely, the anti-bacterial agent automatically returns to an inactive state when the first hook and loop strip is separated from the second hook and loop strip. Thus, the inactive anti-bacterial agent is absorbed into the interior of the body.

Notably, the anti-bacterial agent may be a gel when disposed at the inactive state inside the interior of the body. The anti-bacterial agent may be foam when disposed at the active state outside the interior of the body.

In one embodiment, the first and second hook and look strips are detachably mated together when the body is rolled into a tube shape. Notably, the first and second hook and loop strips preferably include first and second heating elements that are activated upon contact with each other.

The present invention may further include a sensor communicatively coupled to the first and second hook and loop strips; a switch electrically coupled to the sensors; an audio playback device communicatively coupled to the switch; a power source communicatively coupled to the switch and the audio playback device respectively. Notably, the sensor automatically generates first and second signals upon detecting a triggering event at the body, the first and second signals being transmitted to the switch and thereby toggling the switch between open and closed positions for permitting and prohibiting power from reaching the audio playback device respectively.

In one embodiment, the sensor may be a heat-detecting sensor that determines when a temperature of the body is above and below a threshold temperature. Such first and second signals are automatically generated and transmitted to the switch when the detected body temperature rises above and below the threshold temperature.

In one embodiment, the sensor may be a pressure-detecting sensor that determines when a pressure exerted against the body is above and below a threshold pressure level. Such first and second signals are automatically generated and transmitted to the switch when the detected body pressure exerted against the outer surface of the body rises above and below the threshold pressure level.

The present invention may further include a method of utilizing a protective handle sheath for covering an existing appliance handle. Such a method preferably includes the chronological steps of: providing a body; providing and impregnating a heat-activated anti-bacterial agent within the body; providing and attaching first and second hook and loop strips to oppositely situated first and second longitudinal edges of the body respectively; and wrapping the body about the existing appliance handle.

The method may further include the chronological steps of: engaging the first and second hook and loop strips to each other; the first and second hook and loop strips generating and transferring heat through the body and thereby transforming the anti-bacterial agent from an inactive state to an active state; directly contacting the anti-bacterial agent to an outer surface of the existing appliance handle by releasing the anti-bacterial agent out from an interior of the body; the anti-bacterial agent automatically returning to an inactive state by separating the first hook and loop strip from the second hook and loop strip; and absorbing the inactive anti-bacterial agent into the interior of the body. Notably, the anti-bacterial agent is a gel when disposed at the inactive state inside the interior of the body, whereas the anti-bacterial agent is foam when disposed at the active state outside the interior of the body.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
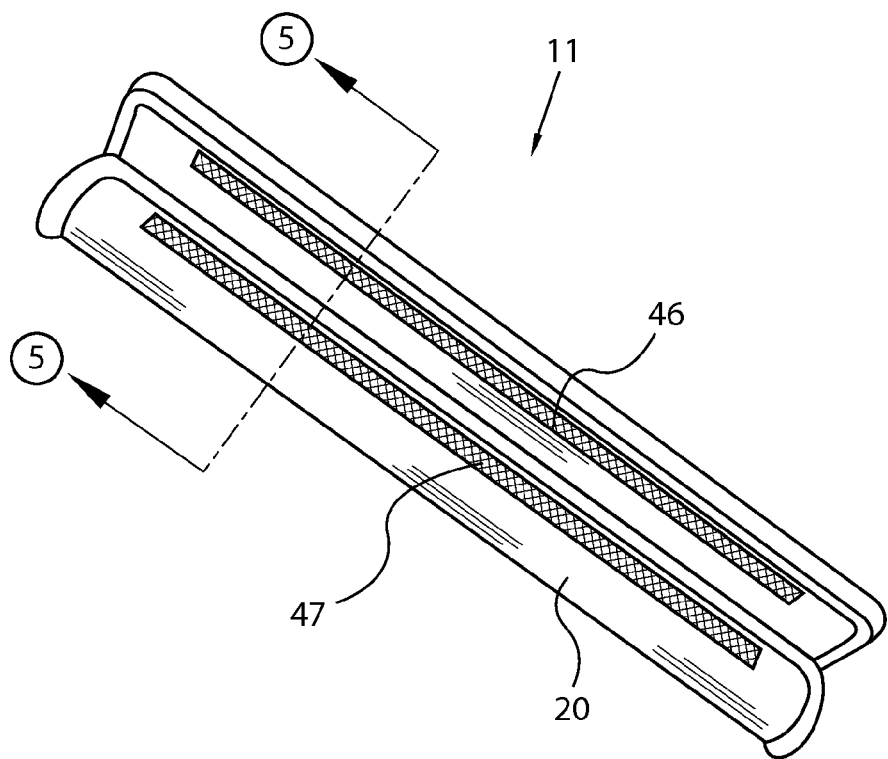
FIG. 1 is a perspective view showing a protective handle sheath, in accordance with the present invention.
Figure 2:
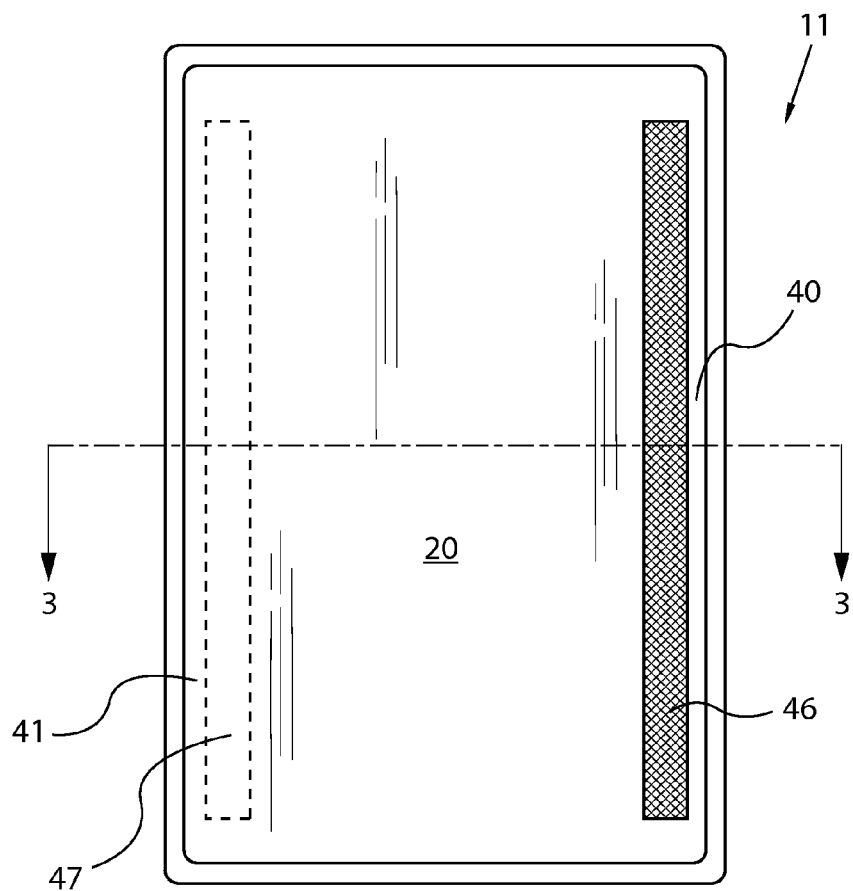
FIG. 2 is a top plan showing the handle sheath at an unrolled position.
Figure 3:
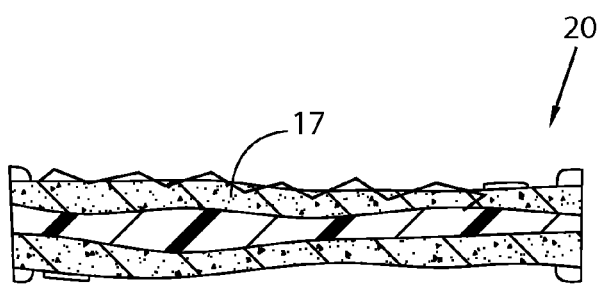
FIG. 3 is a cross-sectional view taken along line 3-3 in FIG. 2, showing an interior of the body when first and second hook and loop strips are disengaged such that the anti-bacterial agent is maintained at the inactive gel state.
Figure 4:
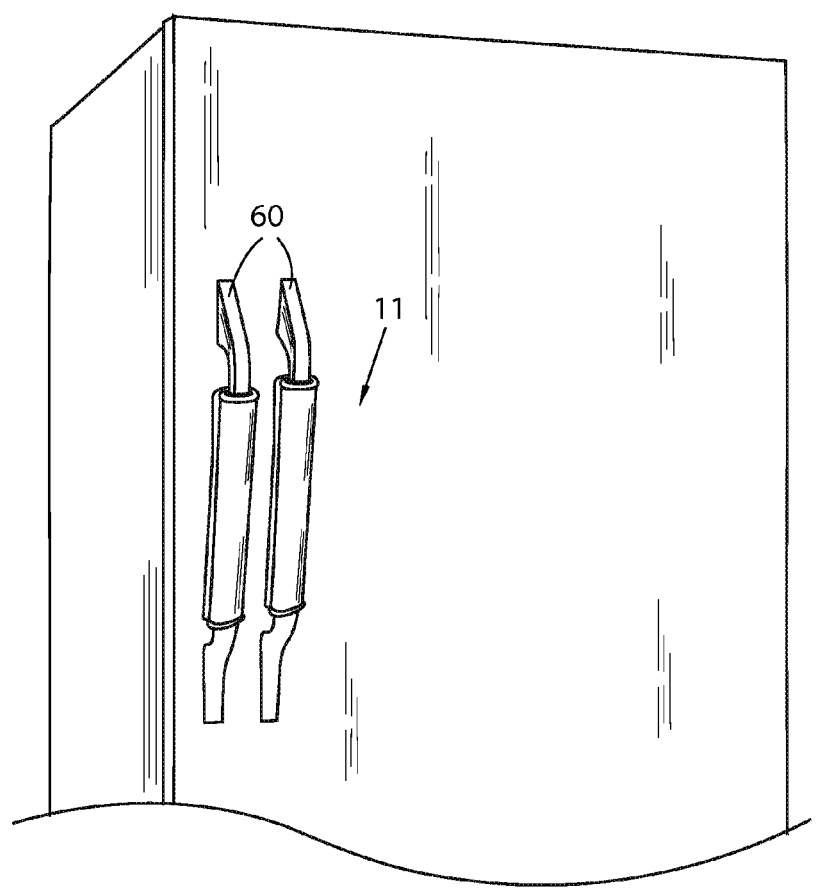
FIG. 4 is a perspective view showing the protective handle sheaths wrapped about the appliance handles.
Figure 5:
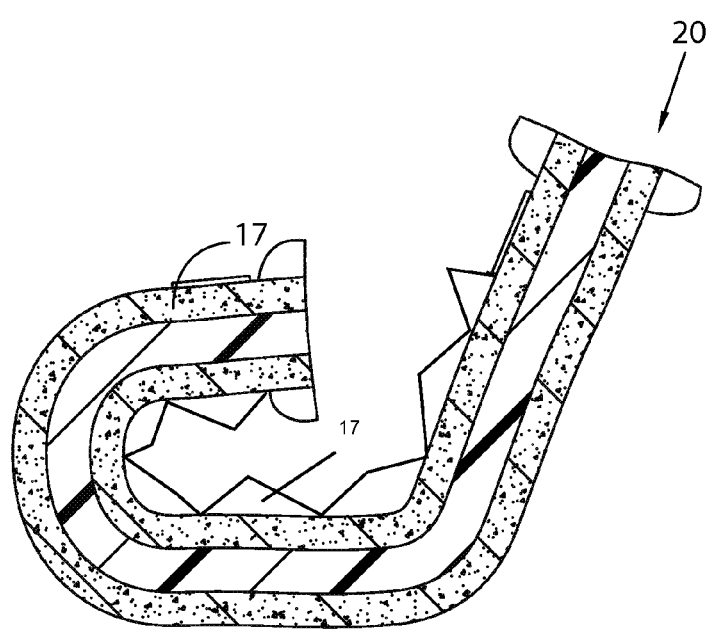
FIG. 5 is a cross-sectional view taken along line 5-5 in FIG. 1, showing an interior of the body when the first and second hook and loop strips are engaged such that heat activates the anti-bacterial agent to its active foam state and thereby egresses from the body.
Figure 6:
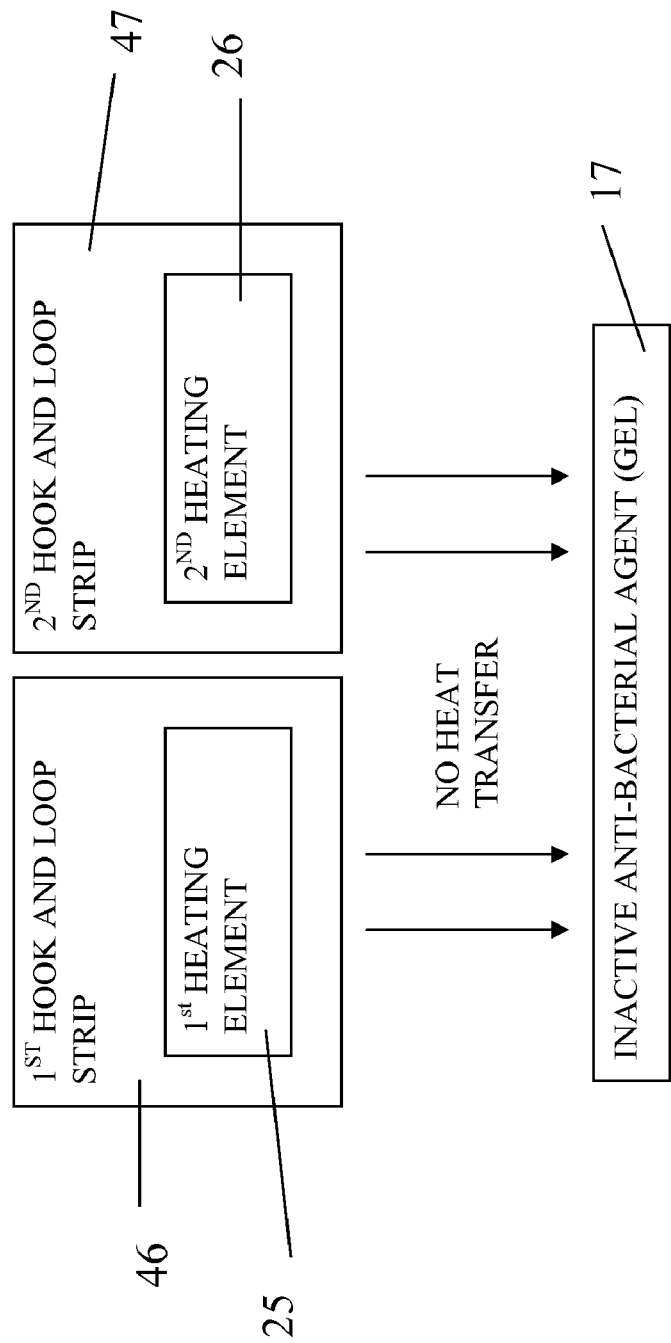
FIG. 6 is a schematic block diagram showing the anti-bacterial agent at an inactive gel state within the body when the first and second hook and loop strips are separated.
Figure 7:
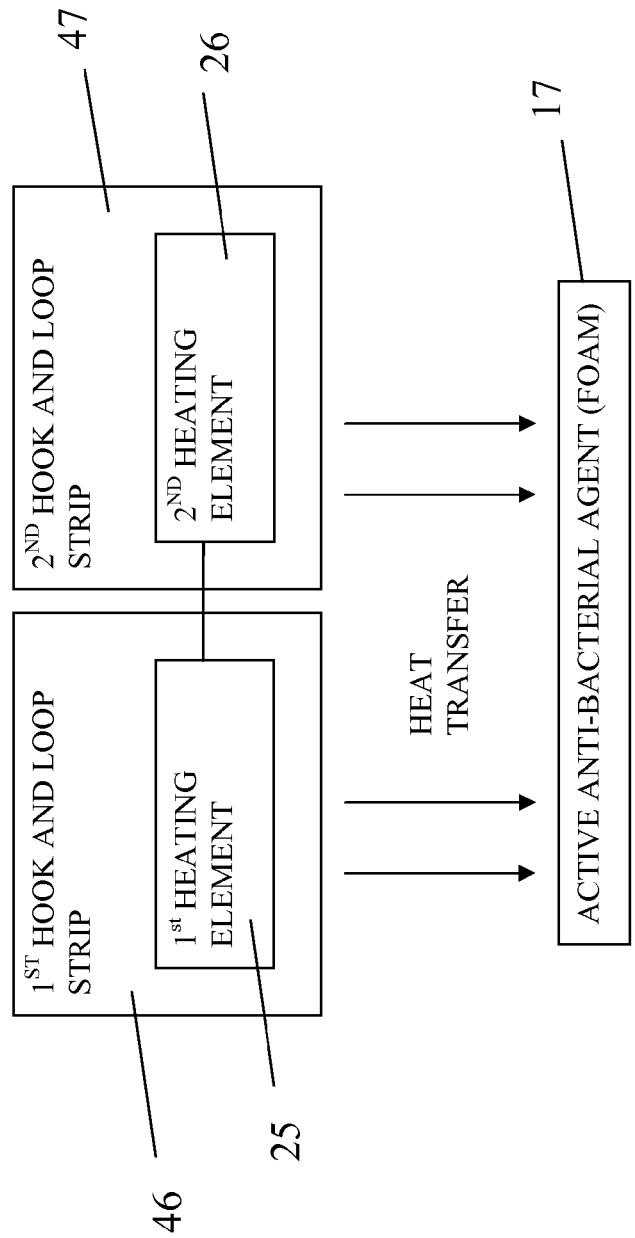
FIG. 7 is a schematic block diagram showing the anti-bacterial agent at an active gel state within the body when the first and second hook and loop strips are attached to each other.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

Referring to FIGS. 1-8, a protective handle sheath 11 includes a body 20 adapted to wrap about the existing appliance handle 60. Such a body 20 may be tubular in shape and may be vertically or horizontally oriented. A heat-activated anti-bacterial agent 17 impregnated within the body 20. Thus, the body 20 is preferably formed from fluid-absorbent foam or other expandable material that can retain fluid similar to a conventional sponge. As an example, a suitable heat-activated anti-bacterial agent may include a non-toxic, aqueous chemical composition that may contain surfactant(s) such as TERGITOL® 15-S-9, d-limonene and/or an emulsifier such as ethoxylated-soybean oil. Such an agent is disclosed in U.S. Pat. No. 7,002,120, for example.

First and second hook and loop strips 46, 47 are attached to oppositely situated first and second longitudinal edges 40, 41 of the body 20 respectively. The strips 40, 41 preferably take the form of a hook and loop members featuring VELCRO® material on the exposed faces. The strips 46, 47 may be attached to the body 20 by means of an adhesive.

Advantageously, the first and second hook and loop strips 46, 47 include first and second heating elements 25, 26 that are activated upon contact with each other. For example, exemplary hook and loop strips 46, 47 may include high-heat acrylic hook and loop fasteners sold by 3M Corporation. Suitable heating elements 25, 26 may include solid heating-generating compositions such as metals having solid surfaces contacts that generate heat when engaged together, well known by one skilled in the art.

The first and second hook and loop strips 46, 47 generate heat when engaged with each other such that heat is transferred through the body 20 and thereby transforms the anti-bacterial agent 17 from an inactive state to an active state. In this manner, the anti-bacterial agent 17 is released out from an interior of the body 20 and thereby adapted to directly contact an outer surface of the existing appliance handle 60.

Conversely, the anti-bacterial agent 17 automatically returns to an inactive state when the first hook and loop strip 46 is separated from the second hook and loop strip 47. Thus, the inactive anti-bacterial agent 17 is absorbed into the interior of the body 20. Notably, the anti-bacterial agent 17 may be a gel when disposed at the inactive state inside the interior of the body 20. The anti-bacterial agent 17 may be foam when disposed at the active state outside the interior of the body 20. The combination of such claimed elements provides an unpredictable and unexpected benefit of minimizing unnecessary anti-bacterial agent residue discharge when the handle sheath is at an unwrapped position.

In one embodiment, the first and second hook and look strips 46, 47 may be detachably mated together when the body 20 is rolled into a tube shape. For example, the user may orient the handle sheath 10 in a same manner as the target handle 60. Then, the user may tuck one end of the handle sheath 10 behind the handle 60 with VELCRO® strip 46 facing away from the handle 60. Next, the user may wrap the other end of the sheath 10 around the handle 60 and press the other VELCRO® strip 47 together ensuring a snug fit.

Figure 8:
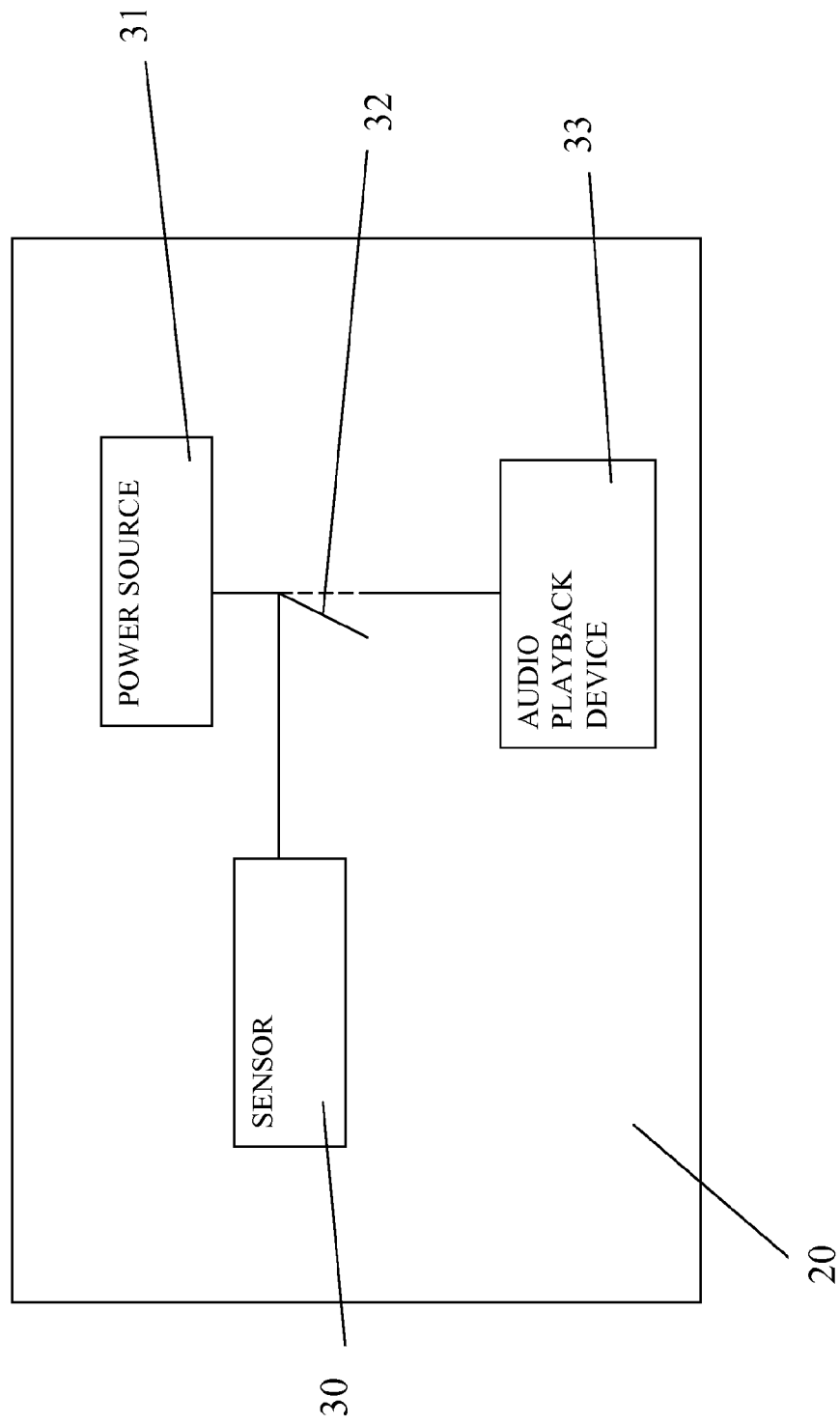
FIG. 8 is a high-level schematic block diagram showing the interrelationship between the major electronic components audio playback system.

Referring to FIG. 8, the present invention may further include a sensor 30 communicatively coupled to the first and second hook and loop strips 46, 47; a switch 32 electrically coupled to the sensor 30; an audio playback device 33 communicatively coupled to the switch 32; a power source 31 communicatively coupled to the switch 32 and the audio playback device 33, respectively. Notably, the sensor 30 automatically generates first and second signals upon detecting a triggering event at the body 20, the first and second signals being transmitted to the switch 32 and thereby toggling the switch 32 between open and closed positions for permitting and prohibiting power from reaching the audio playback device 33 respectively. The combination of such claimed elements provides an unpredictable and unexpected benefit of notifying the user when the body has been moved or when the anti-bacterial agent has been activated, for example.

In one embodiment, the sensor 30 may be a heat-detecting sensor 30 that determines when a temperature of the body 20 is above and below a threshold temperature. Such first and second signals are automatically generated and transmitted to the switch 32 when the detected body 20 temperature rises above and below the threshold temperature.

In one embodiment, the sensor 30 may be a pressure-detecting sensor 30 that determines when a pressure exerted against the body 20 is above and below a threshold pressure level. Such first and second signals are automatically generated and transmitted to the switch 32 when the detected body 20 pressure exerted against the outer surface 22 of the body 20 rises above and below the threshold pressure level.

The present invention may further include a method of utilizing a protective handle sheath 11 for covering an existing appliance handle 60. Such a method preferably includes the chronological steps of: providing a body 20; providing and impregnating a heat-activated anti-bacterial agent 17 within the body 20; providing and attaching first and second hook and loop strips 46, 47 to oppositely situated first and second longitudinal edges 40, 41 of the body 20 respectively; and wrapping the body 20 about the existing appliance handle 60.

The method may further include the chronological steps of: engaging the first and second hook and loop strip 46, 47 to each other; the first and second hook and loop strip 46, 47 generating and transferring heat through the body 20 and thereby transforming the anti-bacterial agent 17 from an inactive state to an active state; directly contacting the anti-bacterial agent 17 to an outer surface 22 of the existing appliance handle 60 by releasing the anti-bacterial agent 17 out from an interior of the body 20; the anti-bacterial agent 17 automatically returning to an inactive state by separating the first hook and loop strip 15 from the second hook and loop strip 16; and absorbing the inactive anti-bacterial agent 17 into the interior of the body 20. Notably, the anti-bacterial agent 17 is a gel 18 when disposed at the inactive state inside the interior of the body 20, whereas the anti-bacterial agent 17 is foam 19 when disposed at the active state outside the interior of the body 20.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A protective handle sheath for covering an existing appliance handle, said protective handle sheath comprising:
   a body adapted to wrap about the existing appliance handle;
   a heat-activated anti-bacterial agent impregnated within said body;
   first and second hook and loop strips attached to oppositely situated first and second longitudinal edges of said body respectively;
   wherein said first and second hook and loop strips generate heat when engaged with each other such that the heat is transferred through said body and thereby transforms said anti-bacterial agent from an inactive state to an active state, said anti-bacterial agent being released out from an interior of said body and thereby adapted to directly contact an outer surface of the existing appliance handle;
   wherein said anti-bacterial agent automatically returns to an inactive state when said first hook and loop strip is separated from said second hook and loop strip, said inactive anti-bacterial agent being absorbed into said interior of said body.

2. The protective handle sheath of claim 1, wherein said first and second hook and loop strips are detachably mated together when said body is rolled into a tube shape.

3. The protective handle sheath of claim 1, wherein said first and second hook and loop strips comprise: first and second heating elements respectively that are activated upon contact with each other.

4. The protective handle sheath of claim 1, further comprising:
   a sensor communicatively coupled to said first and second hook and loop strips;
   a switch electrically coupled to said sensor;
   an audio playback device communicatively coupled to said switch;
   a power source communicatively coupled to said switch and said audio playback device respectively;
   wherein said sensor automatically generates first and second signals upon detecting a triggering event at said body, said first and second signals being transmitted to said switch and thereby toggling said switch between open and closed positions for permitting and prohibiting power from reaching said audio playback device respectively.

5. The protective handle sheath of claim 1, wherein said sensor is a heat-detecting sensor that determines when a temperature of said body is above and below a threshold temperature, said first and second signals being automatically generated and transmitted to said switch when said detected body temperature rises above and below said threshold temperature.

6. The protective handle sheath of claim 1, wherein said sensor is a pressure-detecting sensor that determines when a pressure exerted against said body is above and below a threshold pressure level, said first and second signals being automatically generated and transmitted to said switch when said detected body pressure exerted against said outer surface of said body rises above and below said threshold pressure level.

7. A protective handle sheath for covering an existing appliance handle, said protective handle sheath comprising:
   a body adapted to wrap about the existing appliance handle;
   a heat-activated anti-bacterial agent impregnated within said body;
   first and second hook and loop strips attached to oppositely situated first and second longitudinal edges of said body respectively;

wherein said first and second hook and loop strips generate heat when engaged with each other such that the heat is transferred through said body and thereby transforms said anti-bacterial agent from an inactive state to an active state, said anti-bacterial agent being released out from an interior of said body and thereby adapted to directly contact an outer surface of the existing appliance handle;

wherein said anti-bacterial agent automatically returns to an inactive state when said first hook and loop strip is separated from said second hook and loop strip, said inactive anti-bacterial agent being absorbed into said interior of said body;

wherein said anti-bacterial agent is a gel when disposed at said inactive state inside said interior of said body;

wherein said anti-bacterial agent is a foam when disposed at said active state outside said interior of said body.

8. The protective handle sheath of claim 7, wherein said first and second hook and loop strips are detachably mated together when said body is rolled into a tube shape.

9. The protective handle sheath of claim 7, wherein said first and second hook and loop strips comprise: first and second heating elements respectively that are activated upon contact with each other.

10. The protective handle sheath of claim 7, further comprising:

a sensor communicatively coupled to said first and second hook and loop strips;

a switch electrically coupled to said sensor;

an audio playback device communicatively coupled to said switch;

a power source communicatively coupled to said switch and said audio playback device respectively;

wherein said sensor automatically generates first and second signals upon detecting a triggering event at said body, said first and second signals being transmitted to said switch and thereby toggling said switch between open and closed positions for permitting and prohibiting power from reaching said audio playback device respectively.

11. The protective handle sheath of claim 7, wherein said sensor is a heat-detecting sensor that determines when a temperature of said body is above and below a threshold temperature, said first and second signals being automatically generated and transmitted to said switch when said detected body temperature rises above and below said threshold temperature.

12. The protective handle sheath of claim 7, wherein said sensor is a pressure-detecting sensor that determines when a pressure exerted against said body is above and below a threshold pressure level, said first and second signals being automatically generated and transmitted to said switch when said detected body pressure exerted against said outer surface of said body rises above and below said threshold pressure level.

13. A method of utilizing a protective handle sheath for covering an existing appliance handle, said method comprising the chronological steps of:

providing a body;

providing and impregnating a heat-activated anti-bacterial agent within said body;

providing and attaching first and second hook and loop strips to oppositely situated first and second longitudinal edges of said body respectively;

wrapping said body about the existing appliance handle;

engaging said first and second hook and loop strips to each other;

said first and second hook and loop strips generating and transferring heat through said body and thereby transforming said anti-bacterial agent from an inactive state to an active state;

directly contacting said anti-bacterial agent to an outer surface of the existing appliance handle by releasing said anti-bacterial agent out from an interior of said body;

said anti-bacterial agent automatically returning to an inactive state by separating said first hook and loop strip from said second hook and loop strip; and absorbing said inactive anti-bacterial agent into said interior of said body;

wherein said anti-bacterial agent is a gel when disposed at said inactive state inside said interior of said body;

wherein said anti-bacterial agent is a foam when disposed at said active state outside said interior of said body.

* * * * *